US008600496B2

(12) United States Patent
Kellum

(10) Patent No.: US 8,600,496 B2
(45) Date of Patent: Dec. 3, 2013

(54) CPR ANALYSIS SYSTEM AND METHOD

(75) Inventor: Michael Kellum, Whitewater, WI (US)

(73) Assignee: Scientific Pathways International, LLC, Lake Geneva, WI (US)

(*) Notice: Subject to any disclaimer, the term of this patent is extended or adjusted under 35 U.S.C. 154(b) by 697 days.

(21) Appl. No.: 12/094,259

(22) PCT Filed: Nov. 20, 2006

(86) PCT No.: PCT/US2006/061108
§ 371 (c)(1),
(2), (4) Date: Jan. 27, 2009

(87) PCT Pub. No.: WO2007/081609
PCT Pub. Date: Jul. 19, 2007

(65) Prior Publication Data
US 2009/0240295 A1 Sep. 24, 2009

Related U.S. Application Data

(60) Provisional application No. 60/738,375, filed on Nov. 18, 2005.

(51) Int. Cl.
A61N 1/00 (2006.01)
(52) U.S. Cl.
USPC .......................................................... 607/5
(58) Field of Classification Search
USPC .......................................................... 607/5
See application file for complete search history.

(56) References Cited

U.S. PATENT DOCUMENTS

| 4,102,332 | A | 7/1978 | Gessman |
| 5,593,426 | A | 1/1997 | Morgan et al. |
| 5,782,878 | A | 7/1998 | Morgan et al. |
| 5,785,043 | A | 7/1998 | Cyrus et al. |
| 5,838,244 | A | 11/1998 | Schmidt et al. |
| 5,913,685 | A | 6/1999 | Hutchins |
| 6,125,299 | A | 9/2000 | Groenke et al. |
| 6,141,584 | A | 10/2000 | Rockwell et al. |
| 6,304,773 | B1 | 10/2001 | Taylor et al. |
| 6,321,113 | B1 * | 11/2001 | Parker et al. .................. 607/5 |
| 6,351,671 | B1 * | 2/2002 | Myklebust et al. ............ 607/5 |
| 6,356,785 | B1 | 3/2002 | Snyder et al. |
| 6,381,492 | B1 | 4/2002 | Rockwell et al. |
| 6,405,083 | B1 | 6/2002 | Rockwell et al. |
| 6,427,083 | B1 | 7/2002 | Owen et al. |
| 6,438,417 | B1 | 8/2002 | Rockwell et al. |
| 6,597,948 | B1 | 7/2003 | Rockwell et al. |
| 6,603,999 | B2 | 8/2003 | SerVaas |
| 6,668,192 | B1 | 12/2003 | Parker et al. |

(Continued)

OTHER PUBLICATIONS

International Search Report issued in application No. PCT/US06/61108 (2007).

Primary Examiner — Christopher D Koharski
Assistant Examiner — Nadia Ahmad
(74) Attorney, Agent, or Firm — Barnes & Thornburg LLP

(57) ABSTRACT

Disclosed is a method and computer program product for analyzing treatment of a sudden cardiac arrest victim. The method includes attaching the victim to an automatic external defibrillator, capturing treatment information about the CPR event, alerting a rescuer of treatment steps, and displaying a chest compression interface based on the treatment information. The chest compression interface may include an event log about various AED, rescuer, and background events and may be used to generate a graphical chest compression chart for simple analysis of the quality of a CPR treatment.

23 Claims, 6 Drawing Sheets

(56) References Cited

U.S. PATENT DOCUMENTS

| | | |
|---|---|---|
| 2002/0087195 A1 | 7/2002 | Hansen |
| 2002/0156503 A1 | 10/2002 | Powers et al. |
| 2002/0169482 A1 | 11/2002 | SerVaas |
| 2003/0167075 A1 | 9/2003 | Fincke |
| 2003/0233129 A1 | 12/2003 | Matos |
| 2004/0015191 A1 | 1/2004 | Otman et al. |
| 2004/0124979 A1 | 7/2004 | Medema et al. |
| 2004/0143298 A1* | 7/2004 | Nova et al. ............. 607/5 |
| 2004/0267325 A1* | 12/2004 | Geheb et al. ............ 607/5 |
| 2005/0027331 A1 | 2/2005 | Bardy |
| 2005/0065557 A1 | 3/2005 | Powers et al. |
| 2005/0070964 A1 | 3/2005 | Hansen et al. |

* cited by examiner

CPR ANALYSIS SYSTEM AND METHOD

CROSS-REFERENCE TO RELATED PATENT APPLICATIONS

This patent application is a U.S. Nationalization of international patent application no. PCT/US2006/061108, filed Nov. 20, 2006, which claims priority under 35 U.S.C. §119 to U.S. Provisional Patent Application No. 60/738,375, filed Nov. 18, 2005, all of which applications are expressly incorporated herein by reference in their entireties.

BACKGROUND

Sudden cardiac death (SCD) is the leading single cause of death in this country. Between 350,000 and 450,000 individuals a year, or more than 1000 per day, fall victim to this disease despite 4 decades of education and systematic interventions, survival rates have not improved: about 95% of SCD victims will die.

Sudden cardiac death (SCD) is the leading single cause of death in this country. Between 350,000 and 450,000 individuals a year, or more than 1000 per day, fall victim to this disease despite 4 decades of education and systematic interventions, survival rates have not improved: about 95% of SCD victims will die.

One tool for conceptualizing the treatment of SCD is the "chain of survival", a concept developed by the American Heart Association. The "chain" depicts of a series of linked activities that positively influence the survival of victims of SCD: (1) Early access (recognize the event, call for help); (2) Early CPR (restore circulation and ventilation); (3) Early defibrillation; and (4) Early ACLS (advanced care including airway control and IV medications).

Weakness in any of these "links" reduces the likelihood that subsequent interventions will be successful and therefore reduces the overall chance of survival. Each link also encapsulates a relatively self-contained set of activities and interventions by a specific subset of the many individuals involved in the care of SCD patients. As appealing as it is, the "chain of survival" fails to depict the interactions between the complex set of specific problems and potential interventions that may be of benefit to an individual case of SCD.

One of the aspects of caring for a victim of SCD is the critical importance of time. SCD occurs suddenly, with little or no warning: the victim simply collapses and blood flow to the heart and brain stops abruptly. The window for initiating treatment is measured in minutes—few survive if treatments are delayed beyond 8-10 minutes. The victim is therefore totally dependent upon the actions of those who witness the cardiac arrest. This is in turn influenced by the location of the event: 15-20% occur in public places (where witnesses are more likely to be present) while the remaining 80-85% occur in private locations, the most common being sites of residence, where only 40% of events are unwitnessed. Survival rates for unwitnessed events are uniformly almost zero.

One approach to this problem is to attach an external device to potential victims that detects an arrest and transmits that information to a medical system, bypassing the need for a human "witness." Another approach is to directly treat the heart rhythm that caused the collapse by using an implanted device that defibrillates the person when appropriate.

The main difficulty with attacking the problem at this "recognition-of-arrest" level is a limited ability to predict beforehand who is at risk. SCD is the presenting symptom in about half of all diagnosed cardiac patients and risk factor analysis (other than surviving a SCD) can predict only 10% of individuals at risk.

When an event is witnessed by a layperson, interventions become available that dramatically improve survival: recognition of the event as a cardiac arrest, activation of the EMS system by calling 911, and provision of "CPR" until help arrives. Recognizing a collapse as a possible SCD depends almost totally upon educational programs aimed at the layperson. Calling for help as soon as possible after recognition may be critical because the majority of survivors of SCD have a cardiac rhythm that responds to defibrillation. Education is also the primary modality for improving performance in this activity; but in specialized settings (e.g. industry, schools, sports events, etc.), pre-planned methodologies similar to fire drills could be developed.

A witness who performs "CPR" dramatically increases the odds of survival. In fact, it is the single most valuable contribution to survival, increasing odds of success up to 4.5×. Some witnesses have received training in CPR but even in communities with decades of public education, the percentage of individuals trained is rarely over 30%. Typically only 15% are trained.

Simplification of layperson (and/or initial responder) CPR training to include only activities that are crucial to survival at the time of their contact with the patient (i.e. to "call 911" and "pump on the chest") should improve the number of willing and competent persons. This simplification should also result in more "CPR" actually being delivered to victims because the breathing component in traditional "CPR" in not only difficult to teach & recall but very difficult to perform adequately. Having to breathe for SCD victims results in many witnesses forgoing any CPR activities. Evidence also indicates that breathing may not only be unnecessary in the initial minutes of an arrest but the effort is indeed detrimental because it takes valuable time away from the crucial activity of circulating blood to the brain and heart.

The 911 dispatchers can, if properly trained, assist callers in the performance of CPR. In some areas, this increases the percent of victims who get "CPR" by up to 20%. What they ask callers to perform and their qualifications to give this assistance are important determinants of success in this endeavor. Many 911 centers have recently simplified their coaching to chest compression only "CPR". By doing so, the time spent in coaching the caller is reduced and the activities the caller is expected to perform are greatly simplified.

Important information that may alter the activities of subsequent responders is not routinely collected from 911 calls: atomic clock accurate time of the call, information about the presence of and possibly adequacy of "CPR" being performed by the layperson (with and without coaching); timing of CPR activities. At the present time, this information is almost universally not available to assist in decisions by subsequent rescuers. There is a need for collection and utilization of such data.

Another very practical issue, however, is how many dispatch centers have individuals trained in this activity ("EMD" dispatchers). Without this training, not only may SCD victims go unrecognized, but callers will not be coached to perform "CPR". There is a need to provide non-EMD dispatch centers with a methodology for providing this service to their callers and appropriate feedback to the dispatch center for dispatching functions.

The majority of survivors of SCD are those with a witnessed arrest and whose initial rhythm is ventricular fibrillation (VF). With rare exceptions "CPR" does not "save" a victim; rather it decreases the likelihood that VF will deteriorate into much less salvageable cardiac rhythms and increases the probability that VF will respond favorably to defibrillation (by providing blood flow to the heart). Chest compressions, especially continuous chest compressions, also provide blood flow to the brain and therefore increase the probability of neurologically normal survival.

"Early defibrillation" is a specific link in the "chain of survival." Recent evidence indicates that this dictum may not be scientifically sound during all phases of a cardiac arrest. The provision of "CPR" prior to defibrillation dramatically improves survival (from 4% to 22% in a well designed human study) if the victim has been "down" for 5 minutes or more. The decision to shock first or deliver "CPR" therefore depends upon the time interval between collapse (the usual surrogate used is the time 911 was called because collapse time is very difficult to ascertain accurately) and when the defibrillator is applied to the patient.

This information is not currently utilized in instructions given by automatic external defibrillators (AEDs) because it is not available to the logical units used by the AED. There is a need for providing of this information and therefore modifying of AED instructions, where possible. This applies to AED units that are not part of the formal emergency medical system (EMS) response and therefore are utilized without direct communications with a medical control system.

Defibrillation by agents of the EMS response should, if local protocol permits it, also be preceded by an adequate period of "CPR". Should "CPR" be performed in this particular case, what type of "CPR", and for what period of time according to local protocol should be communicated to the responder. There is a need for provision and documentation of such advice is one component of this disclosure.

The most common method for presenting the results of cardiac arrest cases is one that categorizes patients according to a standardized set of definitions known as the "Utstein" criteria. This methodology includes a graphic presentation of the number of cases in successively more restrictive criteria. Its use permits relatively standardized comparisons between populations being studied because it includes categorization according to clinically relevant determinants.

However, when attempting to analyze the care delivered an individual cardiac arrest case, the Utstein approach has a number of significant limitations. It does not include an analysis of the timing of interventions and activities and therefore the potential time-related interactions of these activities is not addressed. Furthermore, it is for the most part a retrospective analytic methodology. An analysis and presentation of an individual arrest is therefore not available either in real-time or even shortly after the cardiac arrest treatments have been completed.

The present disclosure addresses the limitations of the Utstein methodology of analysis by expanding the nature and format and methodologies of data captured for an arrest. It also modifies the methodology and timing of the feedback to rescuers and reviewers of an arrest.

Additional features and embodiments will become apparent to those skilled in the art upon consideration of the following detailed description of drawings.

BRIEF DESCRIPTION OF THE DRAWINGS

The present disclosure will be described hereafter with reference to the attached drawings which are given as a non-limiting example only, in which.

Figure 1:
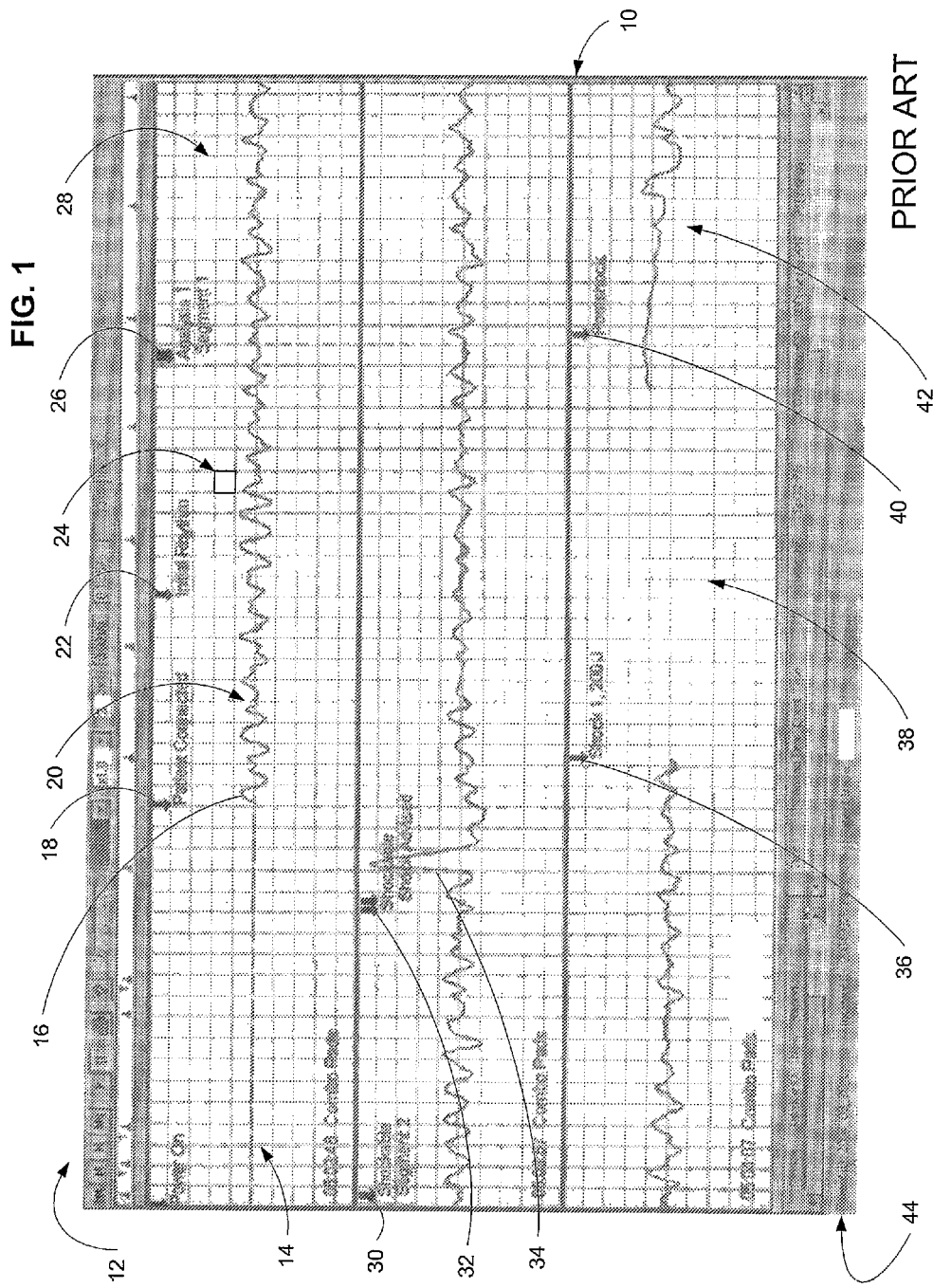
FIG. 1 is a screenshot of a prior art CPR EKG interface.

The exemplification set out herein illustrates embodiments of the disclosure that is not to be construed as limiting the scope of the disclosure in any manner.

DETAILED DESCRIPTION

While the present disclosure may be susceptible to embodiment in different forms, there is shown in the drawings, and herein will be described in detail, embodiments with the understanding that the present description is to be considered an exemplification of the principles of the disclosure and is not intended to be exhaustive or to limit the disclosure to the details of construction and the arrangements of components set forth in the following description or illustrated in the drawings.

Figure 2:
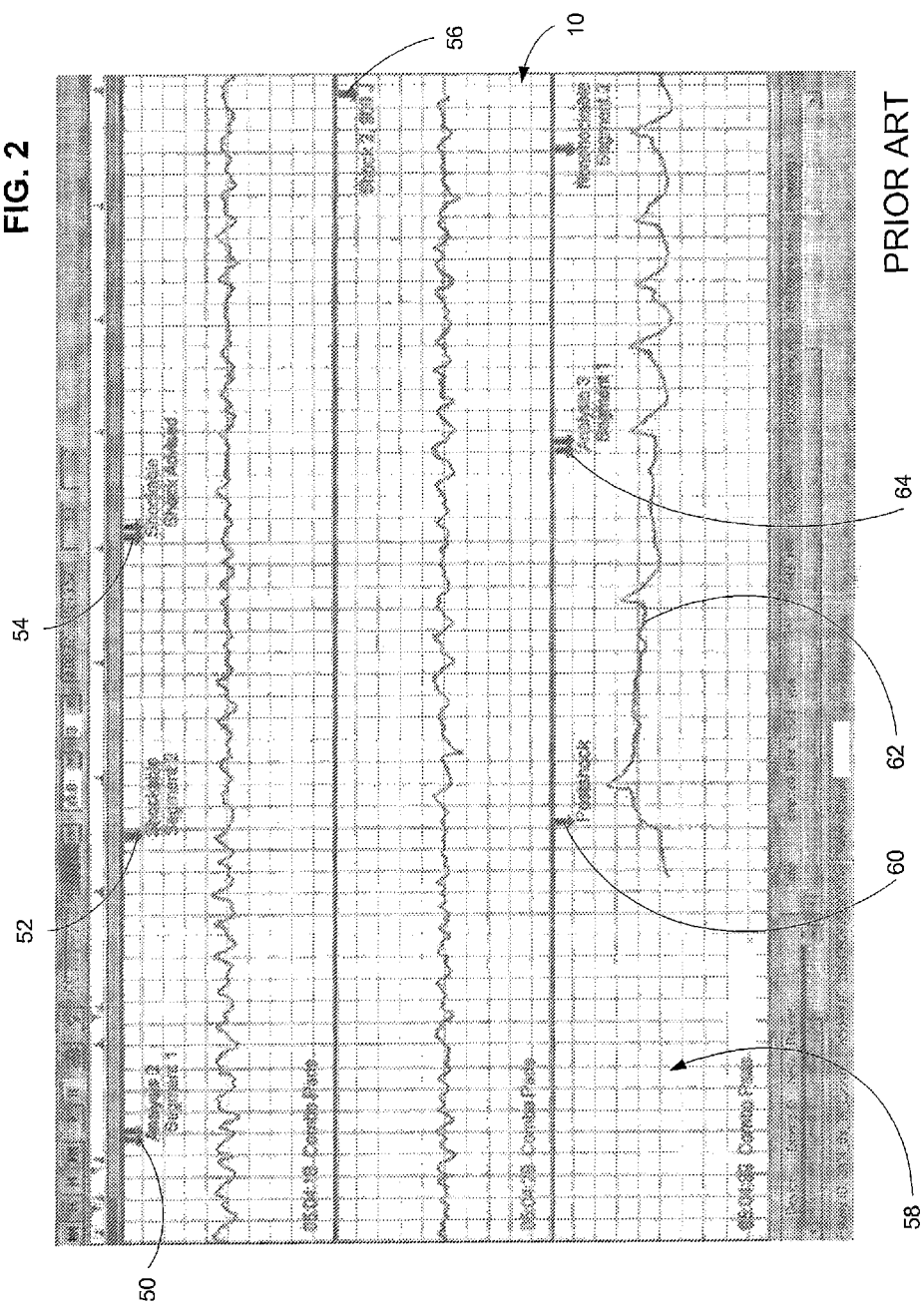
FIG. 2 is a screenshot of the interface of FIG. 1, showing a continuation of an EKG graph shown therein.
Figure 3:
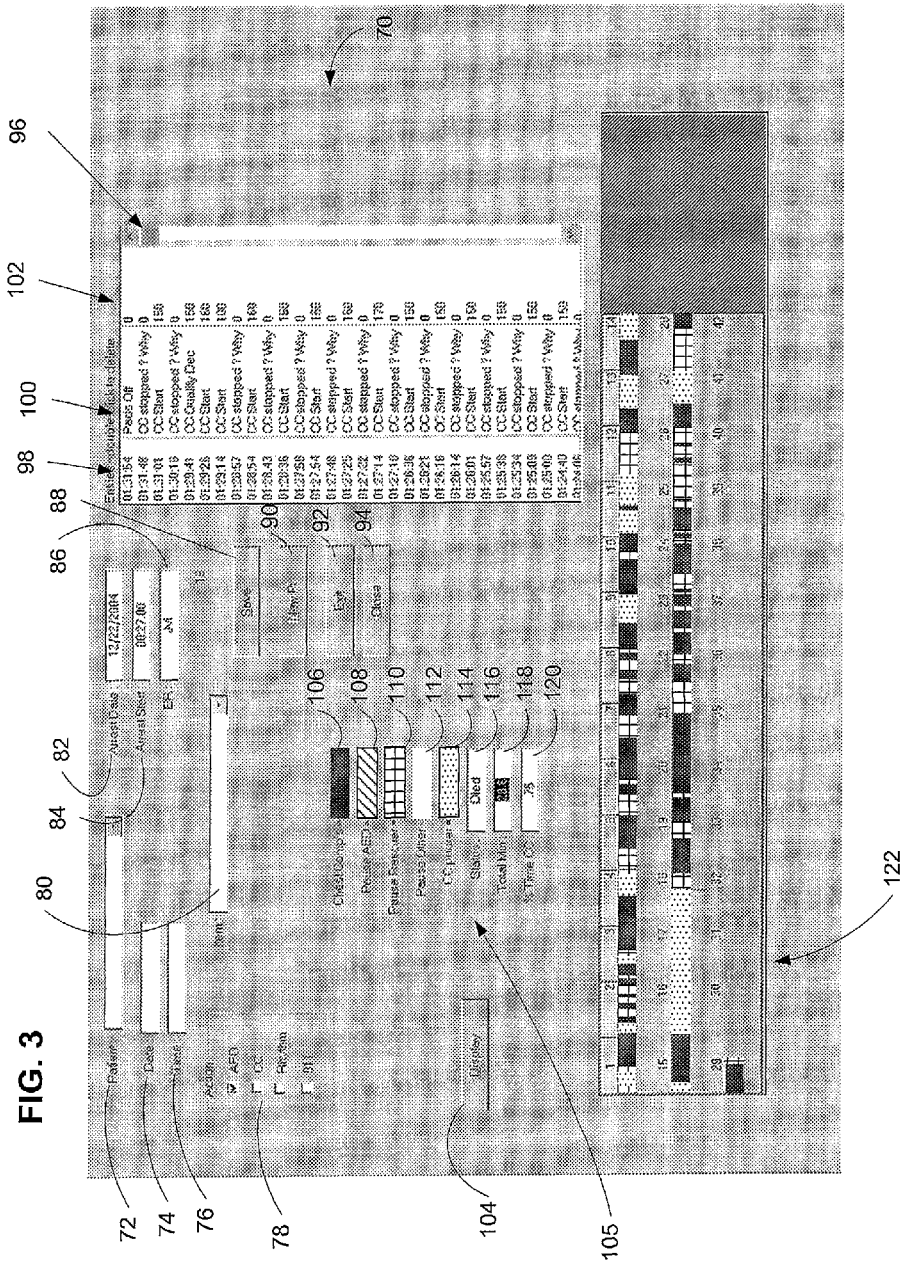
FIG. 3 is a screenshot of one embodiment of a chest compression interface.

FIGS. 1, 2 show prior art interfaces that show EKG (electrocardiogram) information for a patient undergoing treatment for a sudden cardiac arrest, which may be used or otherwise manipulated to produce the chest compression analysis interface shown in FIG. 3. A prior art interface 10, includes a control bar 12 which may include standard controls for moving forward and backward along an EKG graph 14. Once a patient is connected, as depicted along graph 14 at segment 16 corresponding to a patient connected time marker 18, graph 14 begins to display heart rhythms. Various time markers may be used to indicate events recorded by the interface, including an initial rhythm time marker 22. Graph 14 is divided in graphical segments such as a grid, with each grid box 24 representing a selected time interval.

Graph 14 continues to record data through a first analysis segment 28 that begins at an analysis 1 time marker 26. After performing the analysis, a particular segment may be deemed either shockable or non-shockable using algorithms known in the industry. Segments reported or determined to be shockable may appear on interface 10 using time markers such as "shockable" 30 or "shock advised" 32. If the AED that corresponds to the graph 14 administered a shock, that data may appear between a shock time marker 36, and a post shock marker 40 as a gap 38. A post shock segment 42 would then appear for analysis in determining the nature of the resultant heart rhythm.

FIG. 2 is a continuation of FIG. 1, showing additional analysis and shockable event time markers 50, 52, and 54, and administration of an additional shock shown as gap 58 between shock time maker 56 and post shock time maker 60. Additional post shock marker 60, post shock portion 62, and analysis 3 segment maker 64, are also shown.

Interface 10 also includes indicia 44 for identifying the victim and the incident, including patient ID, incident ID, and patient data. This data may be imported or otherwise used in connection with the chest compression analysis interface shown in FIG. 3.

In FIG. 3, a chest compression interface 70 is shown for displaying data that may be used to analyze the chest compression aspect of the quality of sudden cardiac arrest treatment. Interface 70 may generally be a database type interface with a number of fields and data displays corresponding to records for one or more patients, CPR events, or other records. As shown in the exemplary illustrated embodiment, interface 70 includes a patient field 72 which may include the name of the patient, or representative name or code, which may be used, for example, in the event the data is used for aggregate analysis or other analysis where the identity of the patient may need to be kept confidential. HIPAA compliance or other federal, state, or local laws may mandate such steps to keep individually identifiable patient information confidential.

A date field 74 and a time field 76 may also be included for recording a record entry or entry review date and time. An action type selectable check box portion 78 may also be displayed to allow a user to select one or more subsets of CPR-related activities (subsets shown in field 80) to be entered and subsequently displayed. These activities may include, but are not limited to AED use, presence or absence of chest compressions (CC), recording the type and timing of of a heart rhythm data, recording timing of relevant activities of rescuers from 911 or other emergency services communications, recording timing and nature of specific treatments delivered or interventions performed by rescuers or placing a call or otherwise communicating with 911 or other emergency services call or communications centers.

Interface 70 may also include other information about the incident, such as, for example, a cardiac arrest date field 82, arrest start time 84, and information about the rescue worker such as, by way of example, but not limitation, a rescuer's initials, in a field 86. Control buttons may also be included in the interface for file access and the other controls, including for example, a save button 88, a new point button 90, an exit button 92, and a close button 94. Additional buttons that allow the user to modify the color and size and visibility of displayed elements and other configuration settings may be displayed or accessible via interface 70 as well.

Since the times entered in field 76 may be recorded from multiple time sources, a selection of a time source may also be included. A button that takes the user to another form that allows reconciliation these time sources may also be provided.

An event table 96 displaying data entries for the arrest event may also be included in interface 70. Table 96 may include a time column 98, event description 100, and chest compression rate value column 102. Table 96 includes information that may be derived using any available algorithm or recording method from a chart such as one shown in FIGS. 1-2, or be developed from some other recording component that is part of or in communication with an AED or other recording device during the sudden cardiac arrest treatment. A time is logged for the start and stop of each series of chest compressions, along with an explanation, if available, of why the chest compressions stopped. The events listed in field 100 would include all events entered. Deletion of an event and the associated information may be performed as well.

In an embodiment of a sudden cardiac arrest treatment method in which the constant or near-constant application of chest compressions is designated as a high quality treatment, there may be few acceptable explanations for ceasing chest compressions, such as, for example, allowing the AED to analyze the heart rhythm and administer a shock. Other reasons entered would be visible in the fields 96 and 102. When available, information regarding incorrect hand positioning, incorrect compression depth, release of pressure, or other factors that adversely affect the technique of chest compression may be recorded and used in analysis.

A display of chest compression information over the time of an arrest, may also be provided as part of interface 70. Chart 122 may be derived from the data in event table 96. Chart 122 includes a number of colored or otherwise designated segments. A key 105 in FIG. 3 may be provided to explain the segments. Alternatively, clicking on segments of the graph may display information about that particular segment in a pop-up window. The color of individual segments are used to visually present the data displayed. In the illustrated embodiment, a segment during which chest compressions are present 106 may be designated in black. A segment during which the AED is paused 108 may be designated in a selected color such as yellow or with a selected fill pattern such as the pattern shown. A segment during which a rescuer pauses 110 may be designated in another color or stippling pattern. A segment during which a pause in chest compressions occurs for some other reason 112 may be designated in yet another color or stippling pattern. A segment during which the quality of chest compressions is deteriorating or otherwise becoming poorer 114 may be shown in yet another color or stippling pattern. Although the proceeding color and stippling pattern designations are shown and described, other color schemes, patterns in place of colors, or other identification schemes may be used as well and can be customized by a user.

Summary information may also be shown in interface 70, which may include a status fields such as 116, which indicates the outcome of the patient and total minutes field 118 which shows the duration of the recorded event. Other information derived from an analysis of the data, such as field 120 displaying the percentage of time chest compressions were performed, may be present. This may be used in an embodiment where designating the quality of the treatment is based at least in part on a higher percentage of time being spent administering chest compressions. Other analyses of the data, as desired by the user, may be performed.

Figure 4:
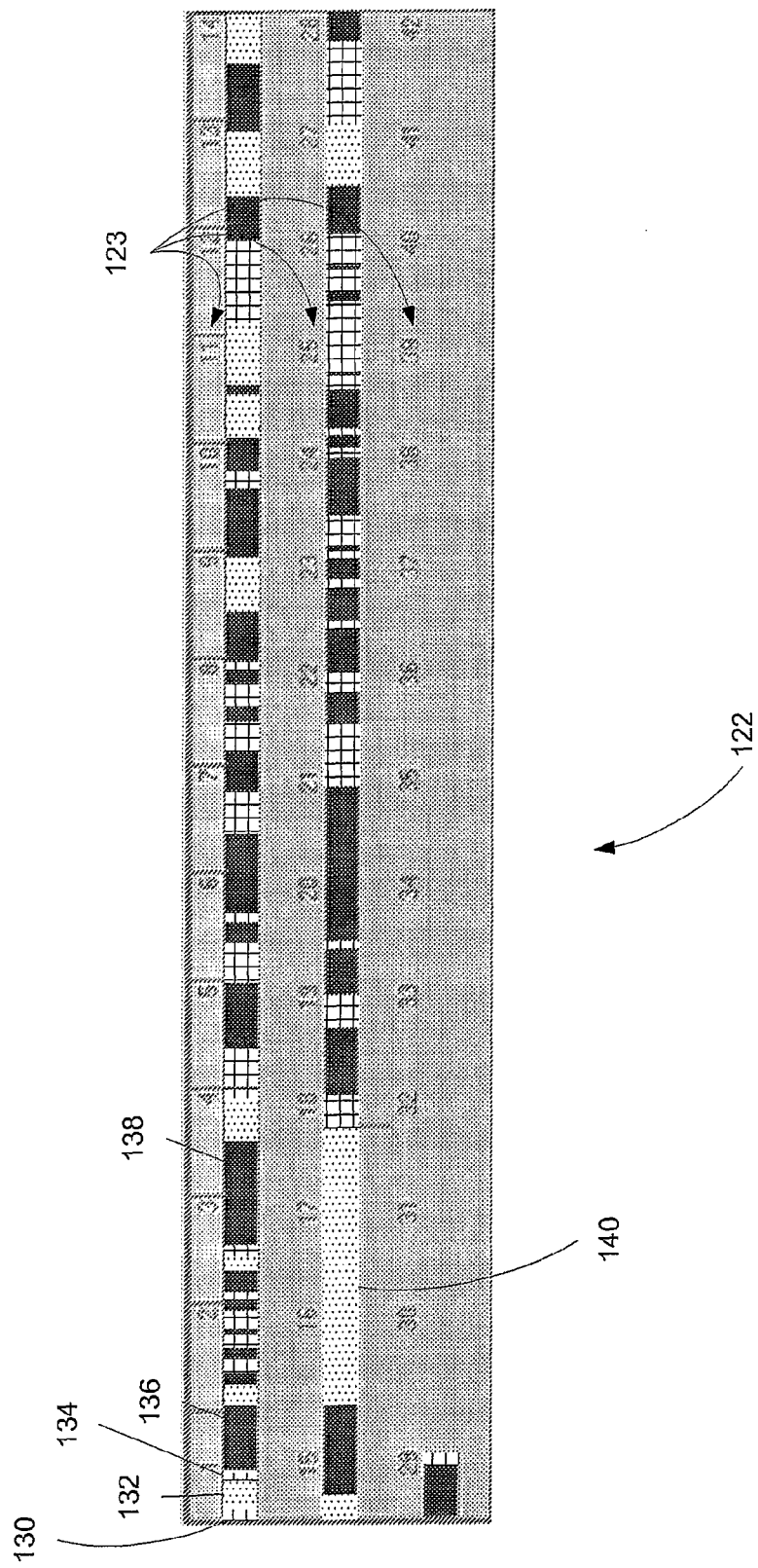
FIG. 4 is a screenshot of one embodiment of a chest compression chart.

FIG. 4 shows a blow-up of chart 122. A timeline 123 includes minutes since the earliest data entry. The actual interval displayed may be selected by the user for evaluation in greater detail. In the illustrated embodiment, a first segment 130 is shown in one color or stippling pattern, meaning no chest compressions were administered by the rescuer by the rescuer's choice. A second segment 132, shown in a second stippling pattern, indicates that poorer quality chest compressions were administered. Segment 136 and 138, for example, shown in black, represent the presence of good chest compressions. These segments or bands would continue to alternate along the timeline corresponding to the events recorded or input into the interface. Again, the choice of colors or stippling patterns used may be set by the operator.

The information displayed in the graph shown in FIG. 4 may be expanded to include that relating to ventilations, specific interventions performed by rescuers, and other relevant timed activities that occurred. Exactly which of these elements are displayed may also be determined by the operator/reviewer using configuration settings.

Information about the quality of the treatment may be garnered by analyzing the graph. For example, segment 140 shows a long period during which poor quality chest compressions were being administered. This may have been, for example, due to rescuer fatigue. A lack of a subsequent long first selected color or stippling pattern band may reasonably show the first rescuer was relieved by a second rescuer. Other analyses may be deduced from the segments as well, which may be used for a variety of purposes, including but not limited to designating a quality for the treatment.

Figure 5:
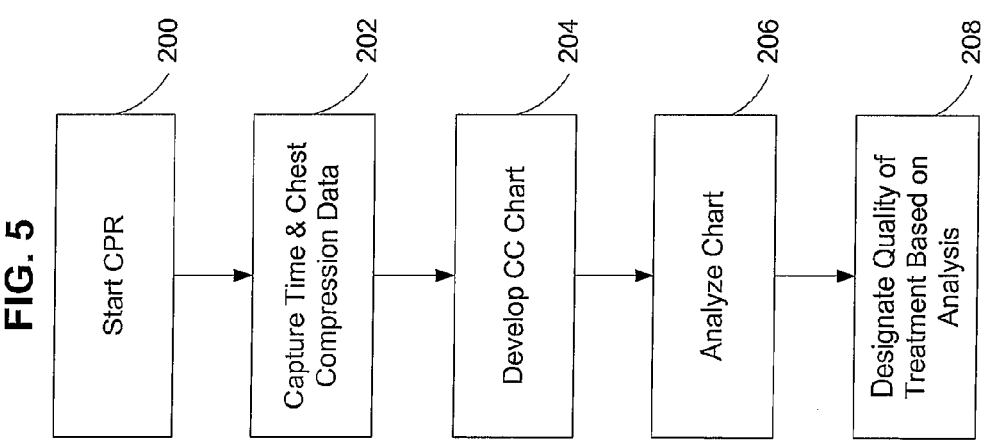
FIG. 5 is a simplified diagrammatic flowchart showing steps in one embodiment of a method of analyzing treatment of a sudden cardiac arrest.

FIG. 5 generally shows the steps in one embodiment of a method of analyzing treatment of a sudden cardiac arrest victim. Generally, a victim is attached to an AED and CPR or other cardiac arrest treatment is started (step 200). The AED may capture data, or communicate data externally, data that is related to the treatment. In the present method, data related to the timing, presence, and/or absence of chest compressions is recorded (step 202). This data may be collected directly from the AED, for example, where the AED has a pressure pad connected thereto for measuring presence and/or quality of chest compressions. A rescuer may be notified, for example, by a speaker, readout, display screen, vibration, or other means to start compressions, stop compressions, be alerted that chest compression quality is deteriorating, increase pressure, decrease pressure, push a different distance into a victim's chest, retract further after compression, or take some other action related to the treatment. Extraneous data may be deleted, ignored, or otherwise filtered out if being gleaned from other charts, such as an EKG chart. The remaining useful data is then used to develop a chest compression chart (step 204), such as chart 122 shown in FIG. 4.

In a next step 206, the chart may be analyzed, such as determining whether quality chest compressions were administered during a sufficient percentage or selected threshold of the treatment. A scale may develop, such as for example, greater than 50% chest compressions corresponding to a high quality treatment. Other scales may be used as well to designate a quality of the treatment (step 208). The designation could in turn be used for a variety of purposes including but not limited to subsequent training of the rescuer performing the treatment or other rescuers, medical malpractice inquiries, insurance coverage, development of better shock algorithms, development of better sudden cardiac arrest treatments, aggregate statistical analysis, and other purposes.

Step 206 may also include analyses where other interventions than chest compressions are considered. The structure of the database and the information collected may permit innovative methodologies for such analyses.

Figure 6:
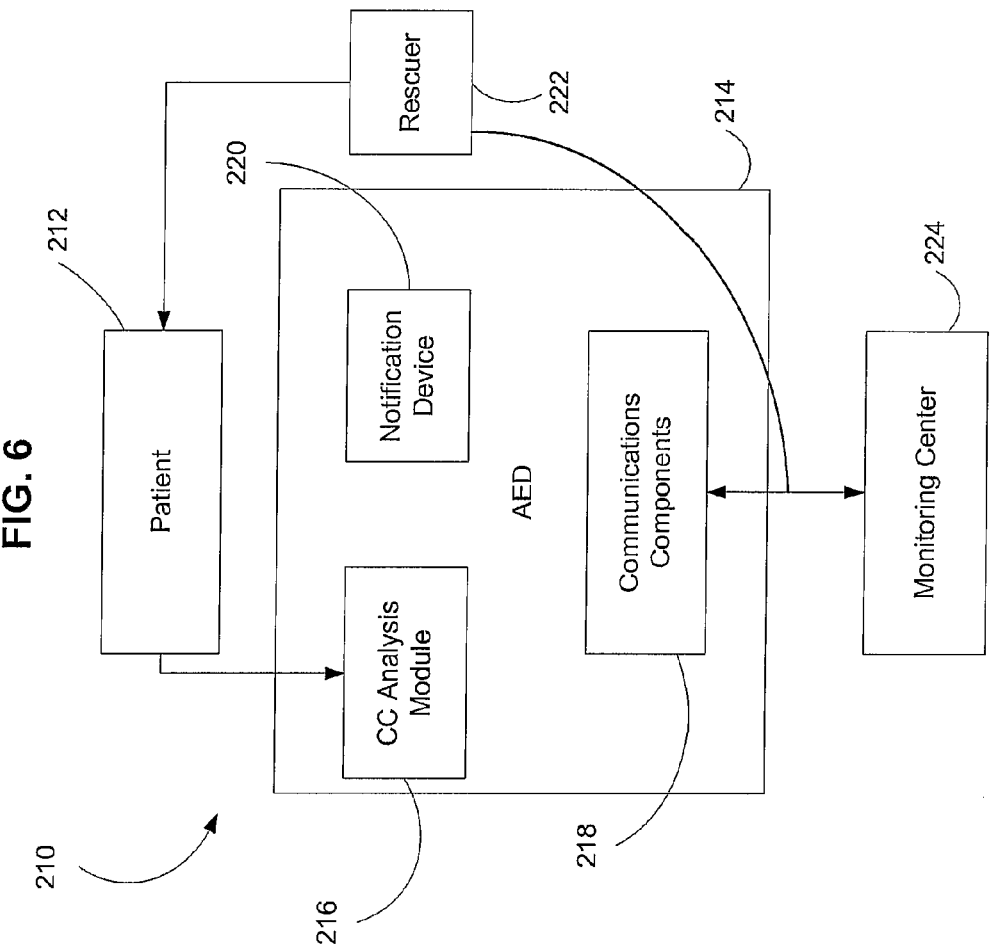
FIG. 6 is a simplified diagrammatic flowchart of a system for analyzing treatment of a sudden cardiac arrest.

One embodiment of the system, as shown in 210, may perform one or more steps of the present method is shown in FIG. 6. A feature of the present system is therefore the involvement of either on-scene processing of multiple inputs or monitoring center processing that interacts back to the rescuer; and in addition collects and records data concerning this. Also, information about other measurable items will be used—eg. impedance measurements that indicate the presence of absence of ventilations. System 210 may include an AED 214 or other treatment device that is connected to a patient or victim 212. It is envisioned that a device for measuring the presence or absence of chest compressions along with a timekeeping function, could be used in place of an AED. A chest compression analysis module may be included in, or be in communication with AED 214. CC analysis module 216 may be some combination of hardware and software that detects the presence or absence, timing, and quality of chest compressions. Any available component may be used including, but not limited to pressure sensitive pads, sensors, or shock paddles.

AED 214 may also include a notification device 220 for alerting a rescuer 222 to a characteristic or proposed action connected to the treatment. Notification device 220 may be, for example, a speaker, readout, indicator, screen display, vibrator or other tactile indicator, or other notification device. One embodiment may, for example, give immediate verbal feedback to the rescuer concerning rates of chest compressions or ventilations or even prompting as to which pharmacologic interventions are indicated given the progress of the arrest to date.

In one embodiment, AED 214 may include one or more communications components 218 for relaying information related to the treatment, such as chest compression data, to a monitoring center 224. Monitoring center 224 may a connected to the 911 or dispatching center over phone lines or be connected over other communications networks such as satellite networks, the Internet, or successor networks. In one embodiment, rescuers could then receive information about the progress or status of the patient or treatment by communicating directly with the monitoring center. This information may, for example, include time since 911 call was received that may be used to determine the priority of interventions according to local protocols. Real-time analyses of the arrest would also permit the monitoring center to randomize patients into ongoing study protocols.

Data may be sent in real time to a professional trained to analyze the progress of the arrest utilizing the graphic displays mentioned, which may included but are not limited to chest compressions.

Communications component 218 may also include a GPS system to provide position information to the call center 224, alert additional rescue services providers (police, ambulance, fire department), or connect the AED to closest or most appropriate call center. Communications components 218 may receive updated program information for reprogramming the AED for tasks such as, for example, flashing the memory with new shock/no shock algorithms, new chest compression intelligence commands, or other programming.

Figure 7:
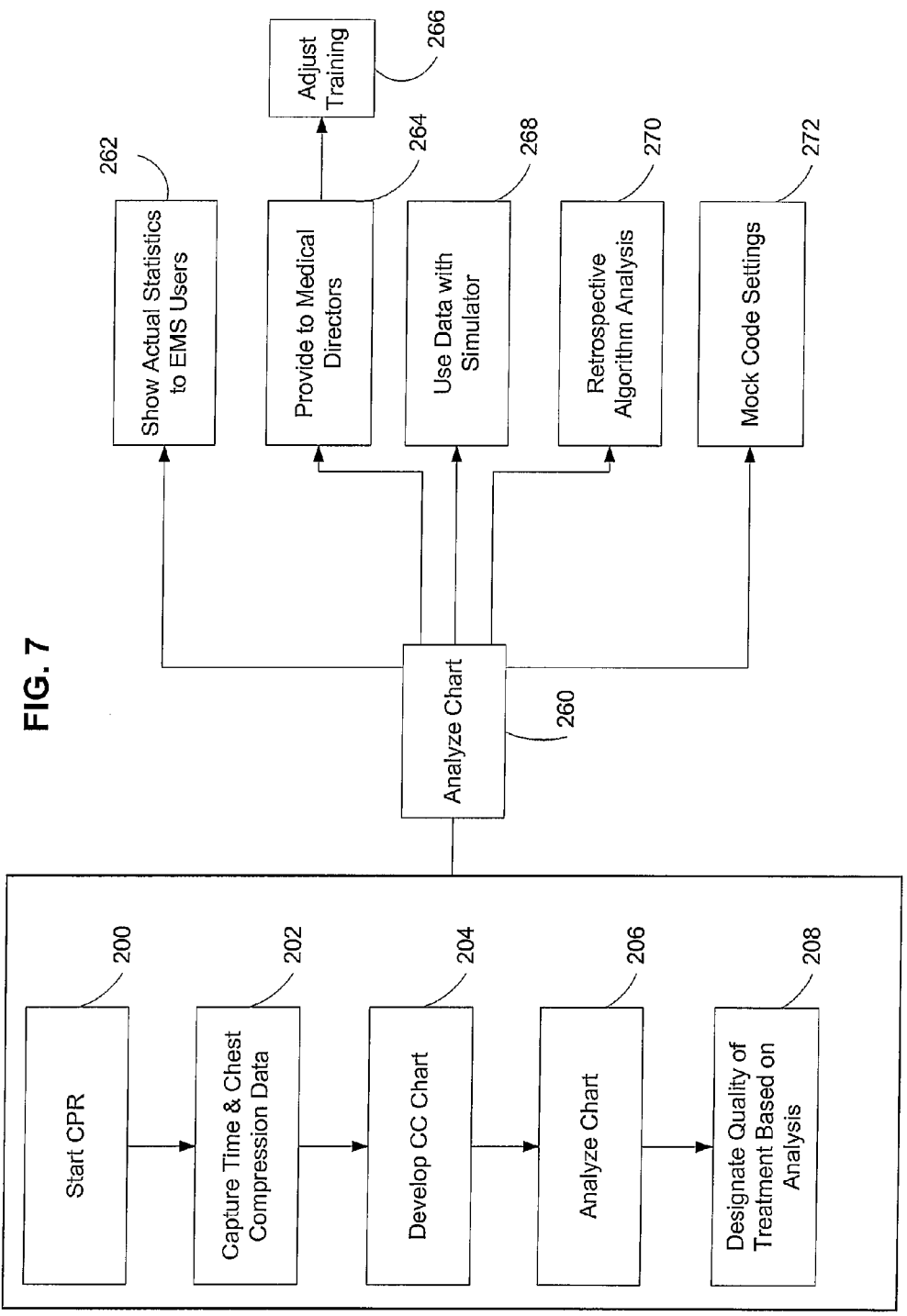
FIG. 7 is a simplified diagrammatic flowchart showing various method of using the chest compression interface in connection with various training methods.

As shown in FIG. 7, the present system and method may be used in connection with training and analysis 260 programs and project. In one embodiment, the method is used in connection with showing actual statistics to EMS squads after an event 262, to go over unusual pauses in chest compressions, unusual timing of interventions, delivery of medication, and the like. Analyses or statistics derived a recorded event may also provide medical directors 264 and the like with information about actual performance so that training programs may be adjusted 266. A simulator 268 may be developed in combination with the graphical display described above to immediately display and critique performance. Analyses may generally be divided into retrospective analysis of codes or algorithms 270, performance analysis, recording, presentation and reporting during code training sessions, and mock code settings 272.

A general purpose computer may be operated by one or more software module having instructions for producing the steps in the method or operating one or more components of the system described above. The software modules may be delivered as a computer program product, such as a computer readable media, downloadable file or set of files, or computer memory product. The term "computer module" or "software module" referenced in this disclosure is meant to be broadly interpreted and cover various types of software code including but not limited to routines, functions, objects, libraries, classes, members, packages, procedures, methods, or lines of code together performing similar functionality to these types of coding. The components of the present disclosure are described herein in terms of functional block components, flow charts and various processing steps. As such, it should be appreciated that such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices. Similarly, the software elements of the present disclosure may be implemented with any programming or scripting language such as Visual Basic, C, SQL, C++, Java, COBOL, assembler, PERL, or the like, with the various algorithms being implemented with any combination of data structures, objects, processes, routines or other programming elements. Further, it should be noted that the present disclosure may employ any number of conventional techniques for data transmission, signaling, data processing, network control, and the like as well as those yet to be conceived.

While embodiments have been illustrated and described in the drawings and foregoing description, such illustrations and descriptions are considered to be exemplary and not restrictive in character, it being understood that only illustrative embodiments have been shown and described and that all changes and modifications that come within the spirit of the invention are desired to be protected. The applicants have provided description and figures which are intended as illustrations of embodiments of the disclosure, and are not intended to be construed as containing or implying limitation of the disclosure to those embodiments. There are a plurality of advantages of the present disclosure arising from various features set forth in the description. It will be noted that alternative embodiments of the disclosure may not include all of the features described yet still benefit from at least some of the advantages of such features. Those of ordinary skill in the art may readily devise their own implementations of the disclosure and associated methods, without undue experimentation, that incorporate one or more of the features of the disclosure and fall within the spirit and scope of the present disclosure and the appended claims.

The invention claimed is:

1. A method of analyzing treatment of a sudden cardiac arrest victim, the method comprising the steps of:
   attaching the victim to an automatic external defibrillator;
   capturing treatment information comprising initial chest compressions;
   alerting a rescuer of treatment steps;
   displaying a chest compression interface based on the treatment information including
   displaying compression quality characteristics and feedback in relation to those characteristics;
   and
   prior to performing the step of defibrillation, recording the treatment information for use in post-event activities.

2. The method of claim 1, the treatment information being one or more of a date, a time, a vital sign, an administration of a chest compression, an administration of medication, and an administration of ventilation.

3. The method of claim 1, the step of alerting a rescuer comprising one or more of an audio alert, a visual alert, and a vibration alert.

4. The method of claim 1, the treatment steps comprising one or more of increasing chest compression pressure, decreasing chest compression pressure, varying a distance of a compression into a chest of the victim, and varying a distance of retraction from the chest of the victim.

5. The method of claim 1, further comprising the chest compression interface including a graphical representation of treatment information.

6. The method of claim 5, further comprising the chest compression interface including a patient identifier field, a date field, a time field, and an event table.

7. The method of claim 6, further comprising the chest compression interface including one or more of a cardiac arrest date field, arrest start time, and a rescue worker identifier.

8. The method of claim 6, further comprising providing a selectable CPR activity check box section to configure the event table to display one or more selected CPR activities.

9. The method of claim 8, further comprising a CPR activity being one or more of an event reported by the automatic external defibrillator, a presence of a chest compression, heart rhythm information, and a communication with an emergency services center.

10. The method of claim 9, further comprising the event table including a time column, event description column, and a chest compression rate value column.

11. The method of claim 10, further comprising the event table including a description column for entering an explanation for discontinuing each chest compression cycle.

12. The method of claim 6, further comprising the chest compression interface including a graphical chest compression chart.

13. The method of claim 12, further comprising deriving the chest compression chart based on data in the event table.

14. The method of claim 12, further comprising the chest compression chart including a number of colored segments, each colored segment corresponding to one of a chest compression, a pause by the automatic external defibrillator, a rescuer pause, a treatment pause, and a poor quality chest compression.

15. The method of claim 14, further comprising analyzing the chest compression chart to designate a quality designation for the treatment of the sudden cardiac arrest victim.

16. The method of claim 15, further comprising designating the treatment as a high quality treatment where the percentage of time chest compressions are administered are over a selected threshold.

17. The method of claim 16, further comprising the selected threshold being 50%.

18. The method of claim 15, further comprising using the quality designation for one or more of subsequent training of the rescuers, medical malpractice inquiries, determining insurance coverage, development shock algorithms, and aggregate statistical analysis.

19. The method of claim 1, further comprising transmitting the treatment information to a monitoring center.

20. The method of claim 19, further comprising the monitoring center transmitting treatment instructions to a rescuer based on the treatment information.

21. The method of claim 19 further comprising the monitoring center transmitting treatment instructions to a rescuer based on a chest compression chart derived from the treatment information.

22. A computer program product having program code stored thereon for analyzing a sudden cardiac arrest treatment, the program code, when executed on a computer, causing the computer to: capture treatment information comprising initial chest compressions, alert a rescuer of treatment steps; display a chest compression interface based on the treatment information displaying compression quality characteristics and feedback in relation to those characteristics; and prior to performing the step of defibrillation, recording the treatment information for use in post-event activities.

23. A system for analyzing a sudden cardiac arrest treatment, the system comprising: an automatic external defibrillator, the automatic external defibrillator including a chest compression analysis module, a notification device, and a communications component; the chest compression analysis module operative to capture treatment information comprising initial chest compressions, alert a rescuer of treatment steps; and display a chest compression interface based on the treatment information displaying compression quality characteristics and feedback in relation to those characteristics; and prior to performing the step of defibrillation, recording the treatment information for use in post-event activities.

* * * * *